United States Patent
Mandelis et al.

(10) Patent No.: US 8,306,608 B2
(45) Date of Patent: Nov. 6, 2012

(54) METHOD AND APPARATUS USING INFRARED PHOTOTHERMAL RADIOMETRY (PTR) AND MODULATED LASER LUMINESCENCE (LUM) FOR DIAGNOSTICS OF DEFECTS IN TEETH

(75) Inventors: Andreas Mandelis, Scarborough (CA); Stephen Abrams, Toronto (CA); Jin-Seok Jeon, Vaughan (CA); Kiran Kulkarni, Toronto (CA); Anna Matvienko, Toronto (CA)

(73) Assignee: Quantum Dental Technologies Inc., Toronto (CA)

( * ) Notice: Subject to any disclaimer, the term of this patent is extended or adjusted under 35 U.S.C. 154(b) by 932 days.

(21) Appl. No.: 11/488,194

(22) Filed: Jul. 18, 2006

(65) Prior Publication Data

US 2007/0021670 A1  Jan. 25, 2007

Related U.S. Application Data

(60) Provisional application No. 60/699,878, filed on Jul. 18, 2005.

(51) Int. Cl.
*A61B 6/00* (2006.01)
*G01N 21/00* (2006.01)
*A61C 1/00* (2006.01)

(52) U.S. Cl. .................. 600/473; 356/237.1; 433/29
(58) Field of Classification Search .................. None
See application file for complete search history.

(56) References Cited

U.S. PATENT DOCUMENTS

| | | | |
|---|---|---|---|
| 5,371,368 A * | 12/1994 | Alfano et al. | 250/341.1 |
| 5,880,826 A | 3/1999 | Jung et al. | |
| 6,584,341 B1 | 6/2003 | Mandelis et al. | |
| 7,148,970 B2 * | 12/2006 | de Boer | 356/497 |
| 2004/0059282 A1 * | 3/2004 | Flock et al. | 604/20 |
| 2004/0236269 A1 * | 11/2004 | Marchitto et al. | 604/22 |
| 2006/0184040 A1 * | 8/2006 | Keller et al. | 600/476 |

OTHER PUBLICATIONS

Nicolaides et al. "Quantitative dental measurements by use of simultaneous frequency-domain laser infrared photothermal radiometry and luminescence." Applied Optics, vol. 41, No. 4, Feb. 1, 2002, pp. 768-777.*

Nicolaides et al. "Novel dental dynamic depth profilometric imaging using simultaneous frequency-domain infrared photothermal radiometry and laser luminescence." J of Biomed Optics, vol. 5, No. 1, Jan. 2000, pp. 31-39.*

(Continued)

*Primary Examiner* — Long V. Le
*Assistant Examiner* — Angela M Hoffa
(74) *Attorney, Agent, or Firm* — Hill & Schumacher

(57) ABSTRACT

There is provided a high-spatial-resolution dynamic diagnostic instrument which can provide simultaneous measurements of laser-induced frequency-domain infrared photothermal radiometric and alternating-current (ac) modulated luminescence signals from defects, demineralization, remineralization and caries in teeth intraorally. The emphasis is on the abilities of this instrument to approach important problems such as the detection, diagnosis and ongoing monitoring of carious lesions and or defects on the occlusal pits and fissures, smooth surfaces and interproximal areas between teeth which normally go undetected by x-ray radiographs or visual examination. The instrument is also able to detect early areas of demineralized tooth and or areas of remineralized tooth as well as defects along the margins of restorations. This capability of inspecting a local spot can be extended to a modulated imaging of sub-surface of target tooth by using a multi-array infrared camera. Two configurations of the instrument are presented.

6 Claims, 10 Drawing Sheets

OTHER PUBLICATIONS

Jeon et al. "Depth profilometric ase studies in caries diagnostics of human teeth using modulated laser radiometry and luminescence." Review of Scientific Instruments, vol. 74, No. 1, Jan. 2003, pp. 380-383.*

Jeon et al. "Diagnosis of Pit and Fissure Caries using Frequency-Domain Infrared Photothermal Radiometry and Modulated Laser Luminescence." Caries Research, vol. 38, No. 6, Nov. 2004, pp. 497-513.*

Kromer, Phillip. "UTiLIA: A PC-Based Lock in Amplifier." Aug. 3, 2002.*

Wei et al. "Integrated Optical Elliptic Couplers: Modeling, Design, and Applications." J of Lightwave Tech, vol. 15, No. 5, May 1997, pp. 906-912.*

International Search Report for PCT/CA2006/001171, 5 pages, Oct. 18, 2006.

Depth profilometric case studies in caries diagnostics of human teeth using modulated laser radiometry and luminescence, Jeon et al, Review of Scientific Instruments, vol. 74, No. 1, Jan. 2003 pp. 380-383.

* cited by examiner

METHOD AND APPARATUS USING INFRARED PHOTOTHERMAL RADIOMETRY (PTR) AND MODULATED LASER LUMINESCENCE (LUM) FOR DIAGNOSTICS OF DEFECTS IN TEETH

CROSS REFERENCE TO RELATED U.S. PATENT APPLICATIONS

This patent application relates to U.S. utility patent application Ser. No. 60/699,878 filed on Jul. 18, 2005 entitled SIMULTANEOUS FREQUENCY-DOMAIN INFRARED PHOTOTHERMAL RADIOMETRY (PTR) AND MODULATED LASER LUMINESCENCE (LUM) APPARATUS FOR DIAGNOSTICS OF DEFECTS IN TEETH, filed in English, which is incorporated herein in its entirety by reference.

FIELD OF INVENTION

The present invention relates to an apparatus based on laser-frequency-domain infrared photothermal radiometry (henceforth referred to as FD-PTR or simply PTR) and frequency-domain luminescence (henceforth referred to FD-LUM, or simply LUM), for detection of dental defects, demineralization and or remineralization of hard tissues, defects around restorations and caries intraorally.

BACKGROUND OF THE INVENTION

Nowadays with the widespread use of fluoride, the prevalence of caries, particularly smooth surface caries has been considerably reduced, but the development of a non-invasive, non-contacting technique which can detect and monitor early demineralization on or beneath the enamel, dentin or root surface or dental restorations is essential for the clinical management of this problem. A novel biothermophotonic technique has been introduced, based on the modulated thermal infrared (black-body or Planck radiation) response of a turbid medium, resulting from radiation absorption and non-radiative energy conversion followed by a small temperature rise.

Thus, PTR has the ability to penetrate, and yield information about, an opaque medium well beyond the range of optical imaging. Specifically, the frequency dependence of the penetration depth of thermal waves makes it possible to perform depth profiling of materials. In PTR applications to turbid media, such as hard dental tissue, depth information is obtained following optical-to-thermal energy conversion and transport of the incident laser power in two distinct modes: conductively, from a near-surface distance (50~500 µm) controlled by the thermal diffusivity of enamel; and radiatively, through blackbody emissions from considerably deeper regions commensurate with the optical penetration of the diffusely scattered laser-induced optical field (several mm).

Trends in improved diagnostic capabilities, coupled with significantly higher optical damage thresholds for tissue, point toward the use of frequency-domain techniques as the next-generation technologies to supplement or replace pulsed laser photothermal or photoacoustic detection with due attention to the physics of the photon propagation in the scattering medium. The use of laser biothermophotonics for dental diagnostics, detection and ongoing monitoring is considered as a promising technique, complementary to the phenomenon of laser-induced fluorescence of enamel or to the fluorescence caused by porphyrins present in carious tissue [R. Hibst, K. Konig, "Device for Detecting Dental Caries", U.S. Pat. No. 5,306,144 (1994)]. The first attempt to apply the depth profilometric capability of frequency-domain laser infrared photothermal radiometry (PTR) toward the inspection of dental defects was reported by Mandelis et al.[A. Mandelis, L. Nicolaides, C. Feng, and S. H. Abrams, "Novel Dental Depth Profilometric Imaging Using Simultaneous Frequency-Domain Infrared Photothermal Radiometry and Laser Luminescence", *Biomedical Optoacoustics. Proc SPIE*, A. Oraevsky (ed), 3916, 130-137 (2000)] and Nicolaides et al.[L. Nicolaides, A. Mandelis, and S. H. Abrams, "Novel Dental Dynamic Depth Profilometric Imaging Using Simultaneous Frequency-Domain Infrared Photothermal Radiometry and Laser Luminescence", *J Biomed Opt*, 5, 31-39 (2000)]. More recently this technology has been used for occlusal pit and fissure [R. J. Jeon C. Han A. Mandelis V. Sanchez S. H. Abrams "Diagnosis of Pit and Fissure Caries using Frequency Domain Infrared Photothermal Radiometry and Modulated Laser Luminescence" Caries Research 38,497-513 (2004)] smooth surface and interproximal lesion detection.

SUMMARY OF THE INVENTION

The present invention provides an apparatus with frequency-domain infrared photothermal radiometry (FD-PTR) and modulated laser luminescence (FD-LUM), as complementary dynamic dental detection and diagnostic tools, for inspecting sound and defective (cracked, carious, demineralized) spots on side surface (smooth surface), top (biting or occlusal) surface,nterproximal contact region between neighboring teeth intraorally and on root surfaces. The device is capable of monitoring ongoing demineralization and or remineralization of various areas of the tooth surface whether in vivo or in vitro. This method can be extended to a modulated imaging of sub-surface of target tooth by using a multi-array infrared camera. In addition this method would include a conventional visible spectral range camera to capture and store images of the tooth surface for ongoing reference. All this information can be stored on a computer hard drive or other types of memory devices including paper print out for retrieval during ongoing monitoring of the patient. In addition, the present technology can be used in conjunction with conventional spectral techniques for dental inspection, such as QLF or OCT in order to expand the range and resolution of subsurface and near-surface detection.

In one aspect of the invention there is provided an apparatus for photothermal radiometry and modulated luminescence for inspection of dental tissues of a patient, comprising:

at least one laser light source for irradiating a portion of a surface of a dental tissue with a modulated laser beam of effective wavelength wherein modulated photothermal radiometric signals and modulated luminescence signals are responsively emitted from said portion of the dental surface;

a first detection means for detecting said emitted modulated luminescence signals, and a second detection means for detecting said emitted modulated photothermal radiometric signals;

a hand held probe head, and a flexible optical fiber bundle having a distal end connected to said hand held probe head, said optical fiber bundle including one optical fiber having a proximal end in optical communication with said light source and a distal end terminated at said hand held probe head for transmitting light from said light source to a patient's dental tissue by a clinician handling said hand held probe head, said optical fiber bundle including a plurality of multi-mode optical fibers having distal ends terminated at said hand held probe head, a first pre-selected number of said multi-mode optical fibers being near-infrared-transmitting optical fibers and having proximal ends optically coupled to said first detection means for transmitting said modulated luminescene signals to said first detection means, and a second pre-selected number of said multi-mode optical fibers being mid-infrared-transmitting optical fibers and having proximal ends optically coupled to said second detection means for transmitting said modulated photothermal radiometry signals to said second detection means;

demodulating means for demodulating said emitted modulated photothermal signals into photothermal phase and amplitude signals and said modulated luminescence signals into luminescence phase and amplitude signals; and processing means for comparing said photothermal phase and amplitude signals to photothermal phase and amplitude signals of a reference sample and comparing said luminescence phase and amplitude signals to luminescence phase and amplitude signals of a reference sample to obtain differences, if any, between said portion of said dental tissue and said reference sample and correlating said differences with defects in said dental tissue.

The present invention also provides a method for detection of defects in dental tissue including erosive lesions, pit and fissure lesions, interproximal lesions, smooth surface lesions and or root carious lesions in dental tissue, comprising the steps of:

a) illuminating a portion of a surface of a dental tissue with at least one wavelength of light using a hand held probe head which is attached to a distal end of a flexible optical fiber bundle, said optical fiber bundle including a first optical fiber having a proximal end in optical communication with a light source which emits at said at least one wavelength, and a distal end terminated at said hand held probe head for transmitting light from said light source to a patient's dental tissue by a clinician handling said hand held probe head, said optical fiber bundle including a plurality of multi-mode optical fibers having distal ends terminated at said hand held probe head and proximal ends optically coupled to said detection means, a first pre-selected number of said multi-mode optical fibers being near-infrared-transmitting optical fibers for transmitting said modulated luminescence signals to said detection means, and a second pre-selected number of said multi-mode optical fibers being mid-infrared-transmitting optical fibers for transmitting said photothermal radiometry signals, wherein upon illumination of said portion of a surface of a dental tissue with at least one wavelength of light modulated photothermal radiometric signals and modulated luminescence signals are responsively emitted from said portion of said surface of the dental surface;

b) detecting said emitted modulated photothermal signals and said modulated luminescence signals;

c) demodulating said emitted modulated photothermal signals into photothermal phase and amplitude components and demodulating said modulated luminescence signals into luminescence phase and amplitude signals; and d) comparing said photothermal phase and amplitude signals to photothermal phase and amplitude signals of a reference sample and comparing said luminescence phase and amplitude signals to luminescence phase and amplitude signals of a reference sample to obtain differences, if any, between said portion of said dental tissue and said reference sample and correlating said differences with defects in said dental tissue.

The present invention also provides a modulated imaging system for imaging dental tissue using modulated photothermal radiometry and luminescence for inspection of dental tissues of a patient, comprising:

at least one modulated laser light source for irradiating a portion of a surface of a dental tissue with a beam of light of an effective wavelength wherein modulated photothermal radiometric signals and modulated luminescence signals are responsively emitted from said portion of the dental surface;

imaging detection means positioned with respect to said dental tissue for detecting images of said emitted modulated photothermal signals and said modulated luminescence signals said imaging detection means including a combined near infrared camera, synchronized with said at least one modulated laser light source for detecting images of emitted modulated luminescence signals and a mid infrared camera for detecting images of said emitted modulated photothermal radiometric signals;

demodulating means for demodulating said images of emitted modulated photothermal signals into images of photothermal phase and amplitude signals and said images of modulated luminescence signals into images of luminescence phase and amplitude signals; and processing means for comparing said images of photothermal phase and amplitude signals to images of photothermal phase and amplitude signals of a reference sample and comparing said images of luminescence phase and amplitude signals to images of luminescence phase and amplitude signals of a reference sample to obtain differences, if any, between said portion of said dental tissue and said reference sample and correlating said differences with defects in said dental tissue;

and image display for displaying said images.

The present invention also provides a method for imaging dental tissue for detection of defects in the dental tissue of a patient, comprising the steps of:

a) illuminating a portion of a surface of a dental tissue with a beam of light of an effective wavelength wherein modulated photothermal radiometric signals and modulated luminescence signals are responsively emitted from said portion of the dental surface;

b) detecting images of said emitted modulated photothermal signals and said modulated luminescence signals;

c) demodulating said images of emitted modulated photothermal signals into images of photothermal phase and amplitude components and demodulating said images of modulated luminescence signals into images of luminescence phase and amplitude signals;

d) comparing said images of photothermal phase and amplitude signals to images of photothermal phase and amplitude signals of a reference sample and comparing said images of luminescence phase and amplitude signals to images of luminescence phase and amplitude signals of a reference sample to obtain differences, if any, between said portion of said dental tissue and said reference sample and correlating said differences with defects in said dental tissue; and e) displaying images representative of defects, if any, of the dental tissue on a computer display.

In one aspect, the present method comprises irradiating the tooth surface with an excitation source (laser) of suitable emission wavelength in the near-ultraviolet—visible—near infrared spectral range;

providing rotational degrees of freedom to the excitation source for inspecting dental or tooth surfaces at various angles;

producing periodic frequency pulses of the laser beam in the range including (but not confined to) dc to 100 kHz;

delivering the radiation and collecting the emission by means of optical fibers or off-axis mirror configuration, generating a baseline signal transfer function, H(f), by obtaining the frequency-scan data from a reference sample with well-known radiometric and dynamic (ac) luminescence properties and frequency response.

comparing by means of amplitude ratios and phase differences healthy, defective, erosion, demineralized or carious dental tissue at various frequencies (e.g. 10 Hz and 1 kHz) for optimal contrast and cancellation of the instrumental frequency response.

performing depth-profilometric caries, demineralized and erosion diagnostics and detection through frequency-scan data acquisition.

storing the data on the area examined to allow comparison of changes in the future, providing a print out or hard copy of the status of the area examined, if the data and clinical expertise indicates the presence of pathology, providing the ability to treat the tooth by using lasers to:

remove the decayed or carious tooth material, remove tooth structure for the placement of materials, prepare the tooth using known principles of tooth preparation design using conventional burs, ultrasonic energy, lasers or other devices for tooth preparation, cure or set a filling material in the tooth preparation restoring the tooth to form and function, using suitable laser-fluence delivery protocols through pulse-waveform engineering, for precise, optimized control of optical radiation delivery and thermal energy generation.

if the data and clinical expertise indicates the presence of demineralization, providing the ability to treat the tooth by using lasers to:

alter the surface or subsurface using a laser, alter the surface or subsurface to allow the uptake of various media to enhance remineralization, apply a medium that will either seal the surface or promote remineralization of the surface cure or set a material on the tooth surface restoring the tooth to form and function, using suitable laser-fluence delivery protocols through pulse-waveform engineering, for precise, optimized control of optical radiation delivery and thermal energy generation.

monitor said interventional alterations in the condition of the tooth by means of combined PTR and LUM monitor the tooth surface for ongoing changes prior to any intervention.

Monitor the tooth surface to demonstrate demineralization in vitro and remineralization after application of various therapies and solutions.

A further understanding of the functional and advantageous aspects of the invention can be realized by reference to the following detailed description and drawings.

BRIEF DESCRIPTION OF THE DRAWINGS

The apparatus for defect detection in teeth according to the present invention will now be described by way of example only, reference being had to the accompanying drawings in which:

FIG. 6b is a blown-up view of the hand held piece in the hand held apparatus of FIG. 6a.

DETAILED DESCRIPTION OF THE INVENTION

The current invention is based on low-fluence photothermal radiometric detection and modulated luminescence microscopy, which detects the emission of infrared radiation from a heated region of the sample without thermally altering it. A temperature oscillation due to modulated heating causes a variation in the thermal emissions, which is monitored using an infrared detector. The temperature modulation allows for thermal energy to reach the surface diffusively (or conductively) from a depth $\lambda_{th}(f) = 2\pi\sqrt{\alpha/\pi f}$ approximately equal to a thermal wavelength, where $\alpha$ is the material thermal diffusivity [$cm^2/s$] and f is the laser beam modulation frequency. In addition, black-body (Planck) radiation is emitted from all depths down to the inverse of the optical attenuation coefficient at the wavelength of laser excitation; the non-reabsorbed portion of this radiation is back-propagated out of the surface of the photo-excited tooth and into a suitable infrared detector carrying information from those depths.

Figure 1:
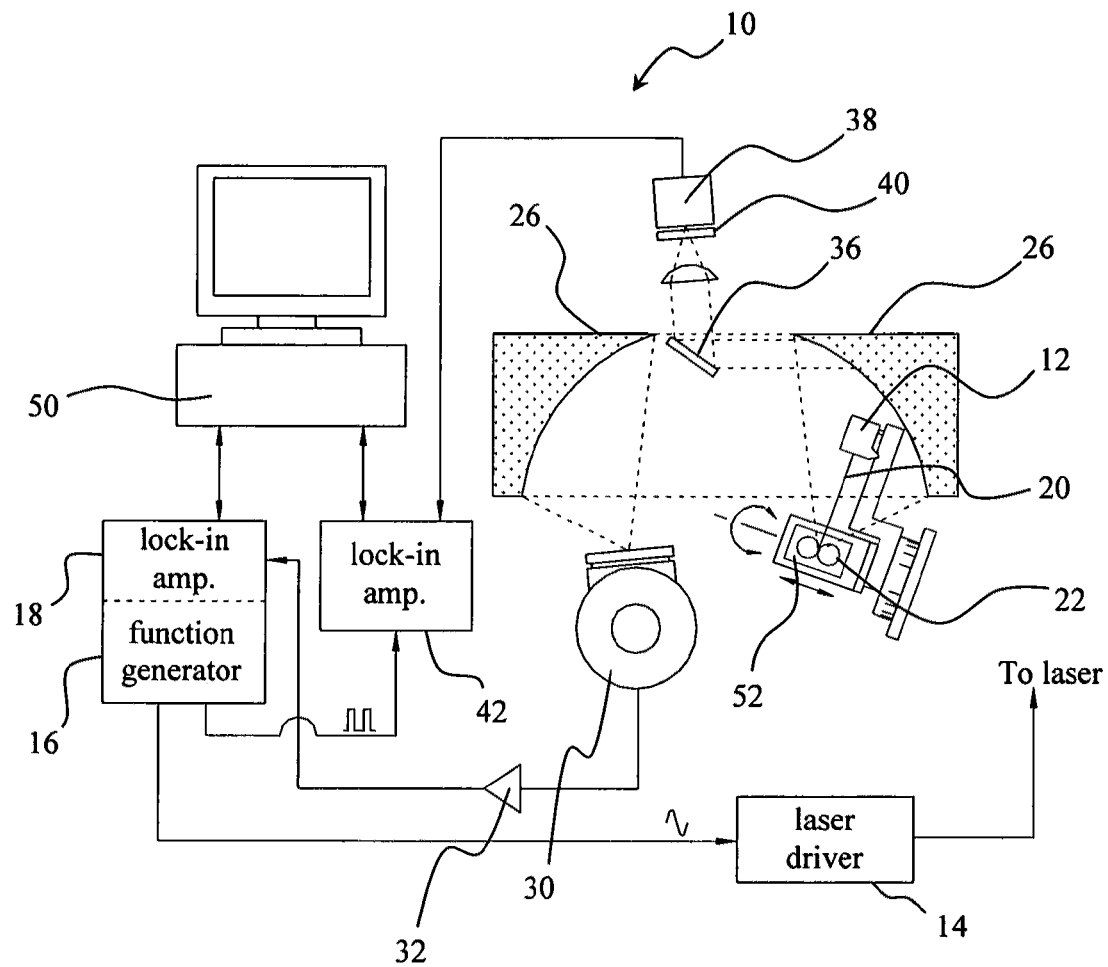
FIG. 1 shows a schematic diagram of a first embodiment of a simultaneous frequency domain infrared photothermal radiometry and frequency domain luminescence instrument for teeth defect detection with added rotational degrees of freedom for the excitation source for inspecting tooth surfaces at various angles according to the present invention.

A schematic diagram of the apparatus is shown generally at 10 in FIG. 1. Semiconductor laser 12 with wavelength 659 nm (e.g. Mitsubishi ML120G21, maximum power 50 mW;) or with 830-nm (e.g. Sanyo DL-7032-001, maximum power 100 mW) is used as the source of both PTR and LUM signals. A diode laser driver 14 (e.g. Coherent 6060) is used for the laser 12 and is triggered by the built-in function generator 16 of the lock-in amplifier 18 (e.g. Stanford Research SR830), modulating the laser current harmonically. The laser beam 20 is focused on the tooth sample 22. The modulated infrared PTR signal from the tooth is collected and focused by two off-axis paraboloidal mirrors 26 (e.g. Melles Griot 02POA019, Rhodium coated) onto an infrared detector 30 such as Mercury Cadmium Telluride (HgCdTe or MCT) detector (e.g. EG&G Judson J15D12-M204-S050U). Before being sent to the lock-in amplifier, the PTR signal is amplified by a preamplifier 32 (EG&G Judson PA-300). For the simultaneous measurement of PTR and LUM signals, a germanium window 36 is placed between the paraboloidal mirrors 26 so that wavelengths up to 1.85 µm (Ge bandgap) would be reflected and absorbed, while infrared radiation with longer wavelengths would be transmitted.

The reflected luminescence is focused onto a photodetector 38 of spectral bandwidth 300 nm~1.1 µm (e.g. Newport 818-BB-20). A cut-on colored glass filter 40 (e.g. Oriel 51345, cut-on wavelength: 715 nm) is placed in front of the photodetector 38 for luminescence to block laser light reflected or scattered by the tooth or root surface or interproximal contact surfaces of the teeth 22. No luminescence data were possible under 830-nm excitation, since photoluminescence emission requires irradiation with higher photons than the peaks of luminescence at ca. 636, 673 and 700 nm [R. Hibst, K. Konig, "Device for Detecting Dental Caries," U.S. Pat. No. 5,306,144 (1994)]. We tested 695-nm and 725-nm filters as well as a 715-nm filter and found the 715-nm filter is optimal for cutting off the laser source (659 nm) and cutting on the luminescence with negligible leakage signal (ca. 190 times less than the minimum dental LUM signals we obtained).

Therefore, the 715-nm cut-on filter 40 is used to measure the luminescence for only the 659-nm laser. For monitoring the modulated luminescence, another lock-in amplifier 42 (e.g. EG&G model 5210) is used. Both lock-in amplifiers 18 and 42 are connected to, and controlled by, the computer 50 via RS-232 or other equivalent ports. A pair of teeth 22 are mounted on LEGO bricks 52. This set up allowed the teeth 22 to be separated and remounted onto the exact position after creating artificial lesions.

The modulated PTR and LUM emissions are then demodulated into photothermal phase and amplitude components and said modulated luminescence signals into luminescence phase and amplitude signals by a lock-in amplifier and processed to compare the photothermal phase and amplitude signals to photothermal phase and amplitude signals of a reference sample and comparing the luminescence phase and amplitude signals to luminescence phase and amplitude signals of a reference sample to obtain differences, if any, between the portion of the dental tissue and the reference sample and correlating these differences with defects in the dental tissue. Further details are disclosed in U.S. Pat. No. 6,584,341 issued Jun. 24, 2003 to Mandelis et al. which is incorporated herein in its entirety by reference.

The apparatus in FIG. 1 provides an optomechanical design which allows for approximal tooth scans with three rotational (angle of the tooth and the mirror, angle of the laser and the tooth, and angle of the incident laser to the tooth) degrees of freedom.

Figure 2A:
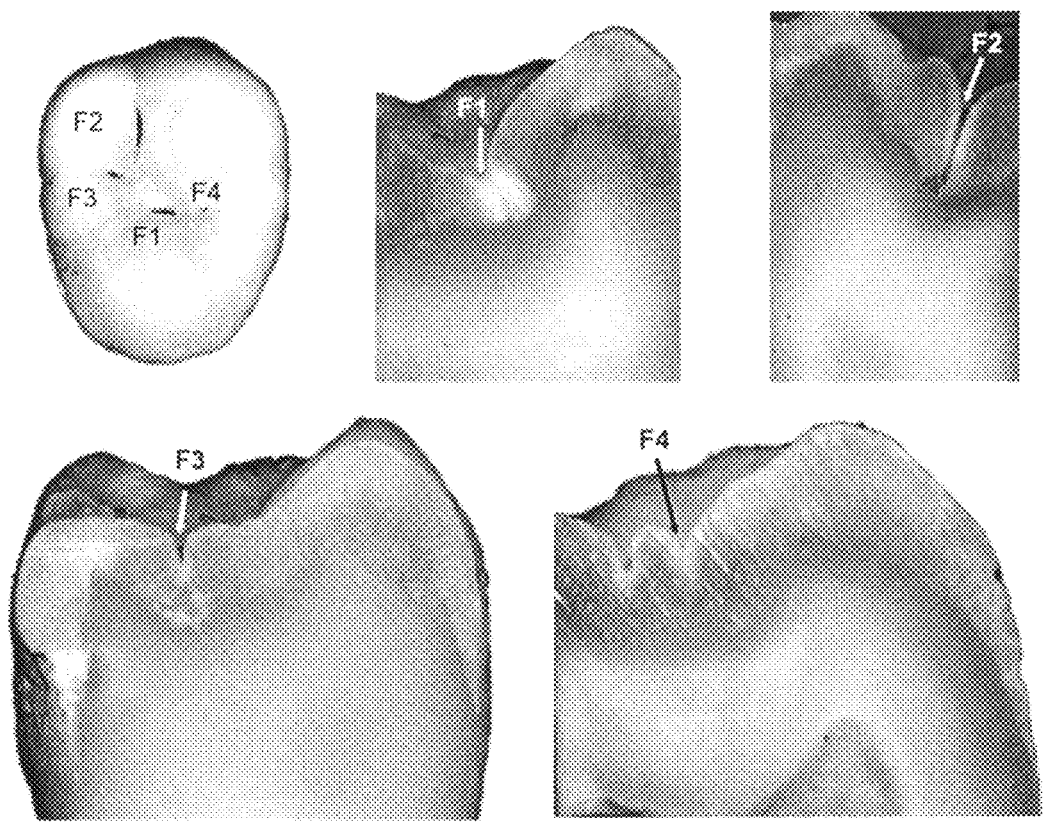
FIG. 2a shows top (biting or occlusal) surface and cross sectional pictures at each measurement point, F1, F2, F3 and F4 of a typical carious lesions in the pits and fissures of a human tooth sample.

FIG. 2 shows a mandibular second premolar illustrating the typical diagnostic and detection ability of PTR and LUM. The tooth had a DIAGNOdent reading of maximum 10 and average visual inspection ranking of 2.2 indicating that a clinician would need to watch or monitor the fissures. There was no indication on the radiographs of any caries being present. Nevertheless, PTR and LUM signals, including all information from the amplitude and phase responses over the entire frequency scan (1 Hz~1 kHz), indicated that measurement spots F2 and F3 have caries into dentin. Histological observation results showed that this is, indeed, the case for these two points, as well as for point F1.

Figure 2B:
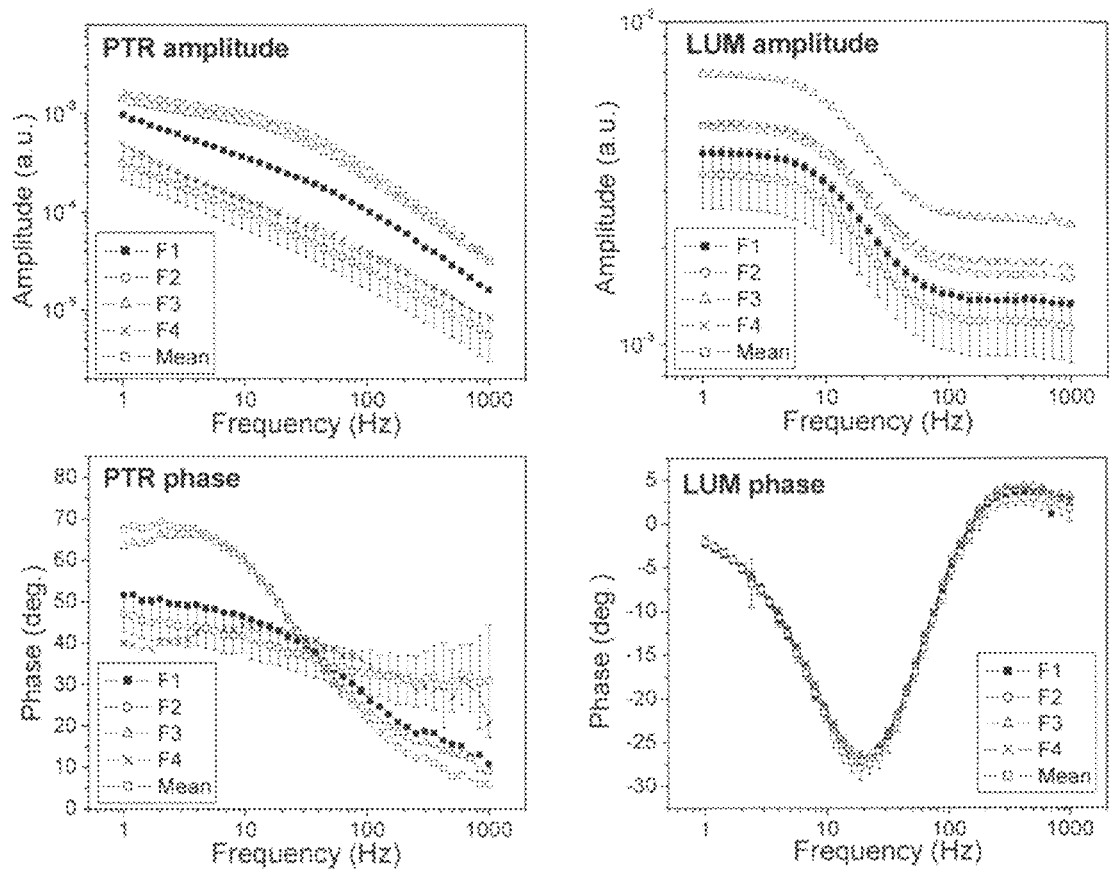
FIG. 2b illustrates typical PTR and LUM responses in the frequency-domain for healthy and carious spots on a human tooth shown in FIG. 2a using 659-nm, 50 mW semiconductor laser excitation.

The signals from fissure F1 show the influence that fissure geometry, angle of the mouth of the fissure or the direction of the fissure base may have in the generation of PTR and LUM signals. The PTR amplitude of F1 in FIG. 2b is above the healthy band and the PTR phase also shows clear departure from the healthy band in the high frequency range. This case illustrates the depth profilometric abilities of PTR. In the case of the slanted, curved carious fissure F1 was illuminated by the incident laser beam in such a way that the carious region formed a thin surface layer, succeeded by a much thicker healthy subsurface enamel layer.

In response, the phase of the PTR signal for F1, in FIG. 2b, falls within the healthy band at low frequencies as expected from the long thermal diffusion length which mostly probes the healthy enamel sub-layer with the carious surface layer as a perturbation to the signal. At high frequencies, however, the (short) thermal diffusion length lies mostly within the carious surface layer and, as a result, the PTR phase emerges below the healthy band above ca. 50 Hz and joins the phases of the carious spots F2 and F3. In principle, the frequency of departure from the healthy band can be used to estimate the thickness of the carious surface layer. PTR and LUM curves of the healthy fissure F4 are located within the healthy band confirming the histological observations.

In order to assess PTR and LUM as caries detection and diagnostic techniques and compare them (combined and separately) to other conventional probes, sensitivities and specificities were calculated at two different thresholds ($D_2$) and ($D_3$) as defined in Table 1 for all the diagnostic methods. While the PTR and LUM signals were taken from all 280 occlusal measurement points, only 1 or 2 points on each tooth were assessed by the other examination methods.

Therefore, each calculation only used the corresponding measurement points. To create suitable criteria for assessing the carious state via PTR and LUM, the general characteristics of the respective signals and their converting equations, listed in Table 2 were used. Those characteristics were established from the experimental results of the frequency scans with carious and healthy tooth samples. In the case of the PTR amplitude, the shape of the frequency scan curve for the healthy spot on a log-log plot is almost linear from low frequency (1 Hz) to high frequency (1000 Hz), while unhealthy spots (demineralized surface, enamel caries or dentin caries) exhibit larger amplitude than healthy spots over the entire frequency range and a pronounced curvature with a "knee" at certain frequency ranges on the logarithmic plot.

The PTR phase shape for the healthy mineralized spot on a linear (phase)-log (frequency) plot is almost linear across all frequencies (1 Hz~1 kHz), while carious spots exhibit larger phases at low frequencies and large slopes, crossing the healthy phase range at intermediate frequencies. There is no difference in the LUM amplitude shape between healthy and carious/demineralized spots. The shape of the amplitude curves is consistent throughout, decreasing from low to high frequencies.

The LUM amplitude curves for demineralized spots lie above the healthy band over the entire frequency range. The LUM phase shows slight differences between healthy points and carious points. In general, carious or demineralized regions exhibit LUM phase lags slightly shifted above the healthy mean throughout the measured frequency range.

Healthy spots may exhibit slight deviations, but only at the high frequency end (>100 Hz).

Establishing the mean values for PTR amplitude and phase, and LUM amplitude and phase from all the healthy smooth enamel surface points on the tooth samples allowed us to examine the behavior of healthy tooth structure without the influence of fissure geometry or the effects of varying enamel thickness in the fissure. A series of mean values and standard deviations vs. frequency curves were developed for each signal and plotted for each tooth. This allowed comparison of the behavior of each probed point to a healthy smooth surface area.

Using these features, characteristic (converting) equations were generated from the plots to yield numeric values defining the state of the teeth as listed in Table 2. In addition, out of the entire frequency scan, each signal (PTR and LUM amplitude and phase) was examined at 3 or 4 frequencies whether it deviated from the healthy norm band, and the number of points that deviated from this band was counted. After calculating all these values, each number group was normalized so that the assigned numbers in each group had a value between 0 for intact teeth and 1 for the worst case of caries. Then these normalized numbers were added and used to evaluate the probed spots. Finally, one value per each measurement point was recorded which included all available information of the frequency response. The thresholds of $D_2$ and $D_3$ were determined by trial and error to comply with the histological observations as closely as possible.

The results of the statistical analysis are given in Table 3. Using the combined criteria of PTR and LUM, the highest sensitivities and specificities, 0.81 and 0.87, respectively, were calculated at the $D_2$ threshold among all the examination methods. In the cases of PTR-only or LUM-only criteria, sensitivities are between 0.52 and 0.69, while specificities are relatively higher, between 0.72 and 0.86. In a manner similar to other findings, visual inspection resulted in poor sensitivities (0.51 at $D_2$ and 0.36 at $D_3$) and particularly high specificities (1.00 at both thresholds). Radiographs also exhibited poor sensitivities (0.29 at $D_2$ and 0.36 at $D_3$) and high specificities (1.00 at $D_2$ 0.85 at $D_3$). The continuous (dc) luminescence method (DIAGNOdent) showed sensitivities of 0.60 at $D_2$ and 0.76 at $D_3$; specificities were 0.78 at $D_2$ and 0.85 at $D_3$. From Table 3 it should be noted, however, that a relatively small subset of all measurement spots was used for obtaining the visual and radiographic statistics, compared to the much more comprehensive sample sizes used for the other methods, especially for PTR and LUM. In addition, DIAGNOdent measurements were performed with that instrument's fiber-optic waveguide, whereas LUM and PTR measurements used direct incidence of the light on the tooth surface and were subject to variable incidence solid angle limitations. This will be improved by introducing fiber-optics as described in FIG. 5.

Figure 3A:
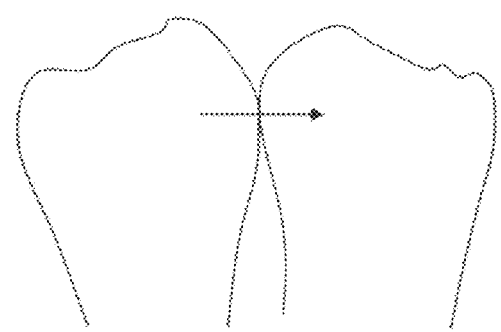
FIG. 3a illustrates a spatially scanned line across the interproximal contact points of two teeth.

FIG. 3 illustrates a sample result of interproximal spatial scans of mechanical hole detection. The samples were stored in saline solution and removed from the container just before the experiments, rinsed thoroughly with tap water for more than 20 seconds, and then left in air for 20 minutes to be dried properly. After the experiments, these samples were immediately placed in the container. Each pair of teeth was mounted on the LEGO bricks and was scanned at 30 Hz from the left to right across the interproximal contact spot as shown with arrows in FIG. 3a. These samples were scanned and radiographed at every step of machining or treatment with an artificial caries agent.

Figure 3B:
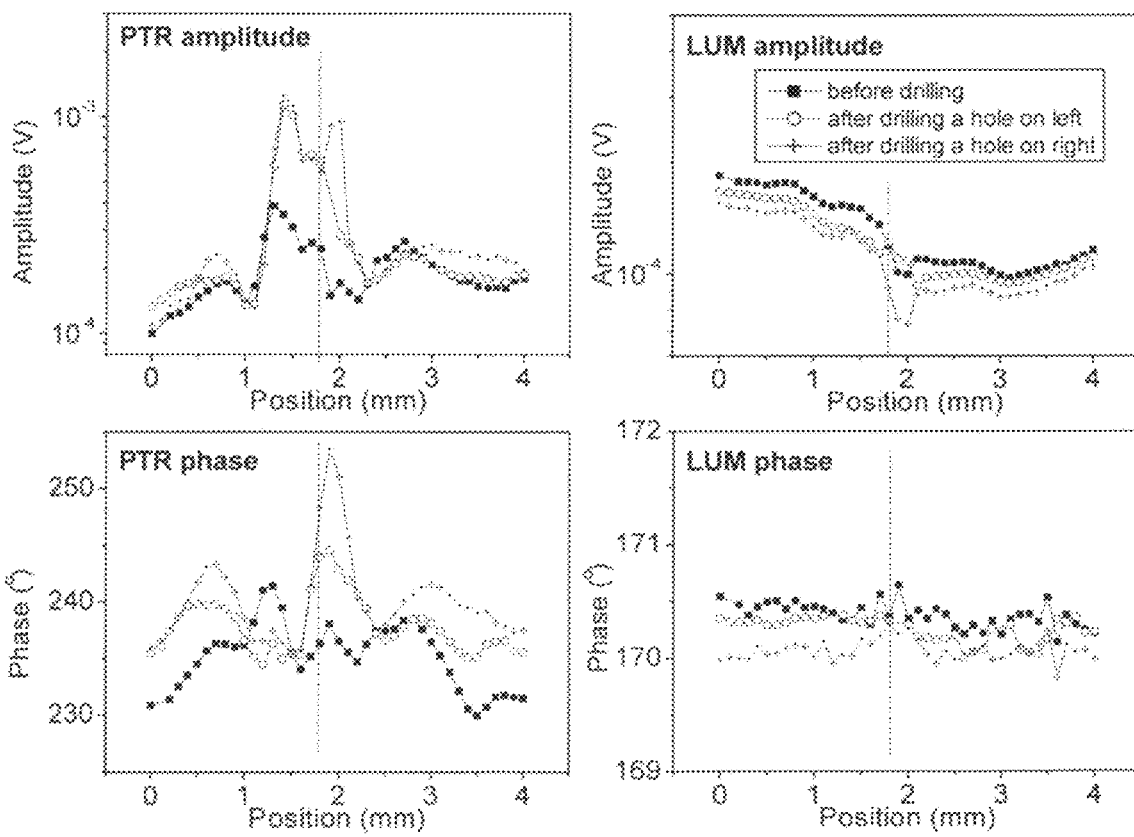
FIG. 3b shows graphs illustrating PTR and LUM responses of spatial scan across the interproximal mechanical holes at a fixed frequency, 5 Hz. The excitation source is a 670 nm, 450 mW semiconductor laser.

In order to see if small artificial holes could be detected by PTR and/or LUM, a ¼ mm round carbide bur was used to make holes with approximately ¼mm depth on the sides of both teeth at the contact location. As shown in FIG. 3b, the left side hole was deeper than that on the right side, so it could be visible on the X-ray image. PTR and LUM signals are shown in FIG. 3b. PTR amplitudes are clearly higher after the sequential drilling of holes, to the left and to the right of the contact point at 1.2~2.3 mm. PTR phases showed big changes at around the holes at 1.5~2.5 mm, too. In the PTR phase, some signal changes also appeared at regions away from the drilled holes, 0~1.5 mm and 2.5~4 mm. It is hypothesized that micro-cracks might have been created due to drilling and caused said signal changes.

The PTR amplitude also showed similar behavior. The LUM amplitude and phase did not show clear differences around the holes because the LUM is essentially a surface phenomenon while the PTR delivers deep sub-surface information. LUM amplitude and phase showed slight decreases at all scans, possibly because LUM is very sensitive to humidity changes.

Figure 4:
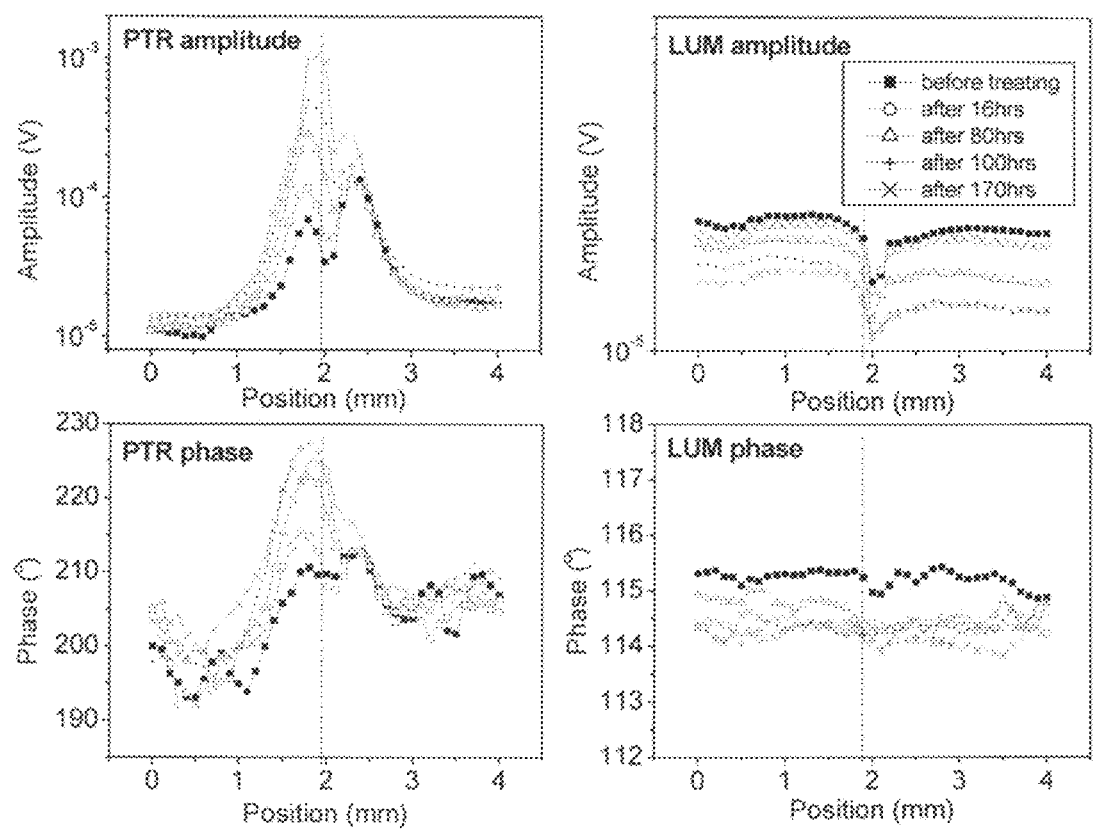
FIG. 4 shows graphs illustrating PTR and LUM responses of spatial scan across the interproximal artificial carious lesion which is created by a demineralization-remineralization solution (2.2 mM potassium phosphate, monobasic ($KH_2PO_4$), 50 mM acetic acid (NaOAc), 2.2 mM of 1 M calcium chloride ($CaCl_2$), 0.5 ppm fluoride ($F^-$), and potassium hydroxide (KOH) for balancing the pH at 4.5) at a fixed frequency, 30 Hz. The excitation source is a 670 nm, 450 mW semiconductor laser.

Another sample set was treated by a demineralization-remineralization solution (2.2 mM Potassium Phosphate, monobasic ($KH_2PO_4$), 50 mM Acetic acid (NaOAc), 2.2 mM of 1 M Calcium Chloride ($CaCl_2$), 0.5 ppm Fluoride ($F^-$), and Potassium Hydroxide (KOH) for balancing the pH at 4~4.5). FIG. 4 shows both PTR amplitude and phase showed clearly monotonic increases after each treatment while LUM was nearly insensitive but for the slight rigid shift (decrease) of the curves across the scanned region believed to be due to humidity changes. Another 7 pairs were treated with the saturated buffer solution and examined in a similar manner except for the treatment time. Each pair was treated over different times; for example, the first pair was treated for only 6 hours and the last pair was treated for 30 days. The lesions created had both mineralized surfaces and demineralized subsurfaces as is found in early carious lesions.

Figure 5A:
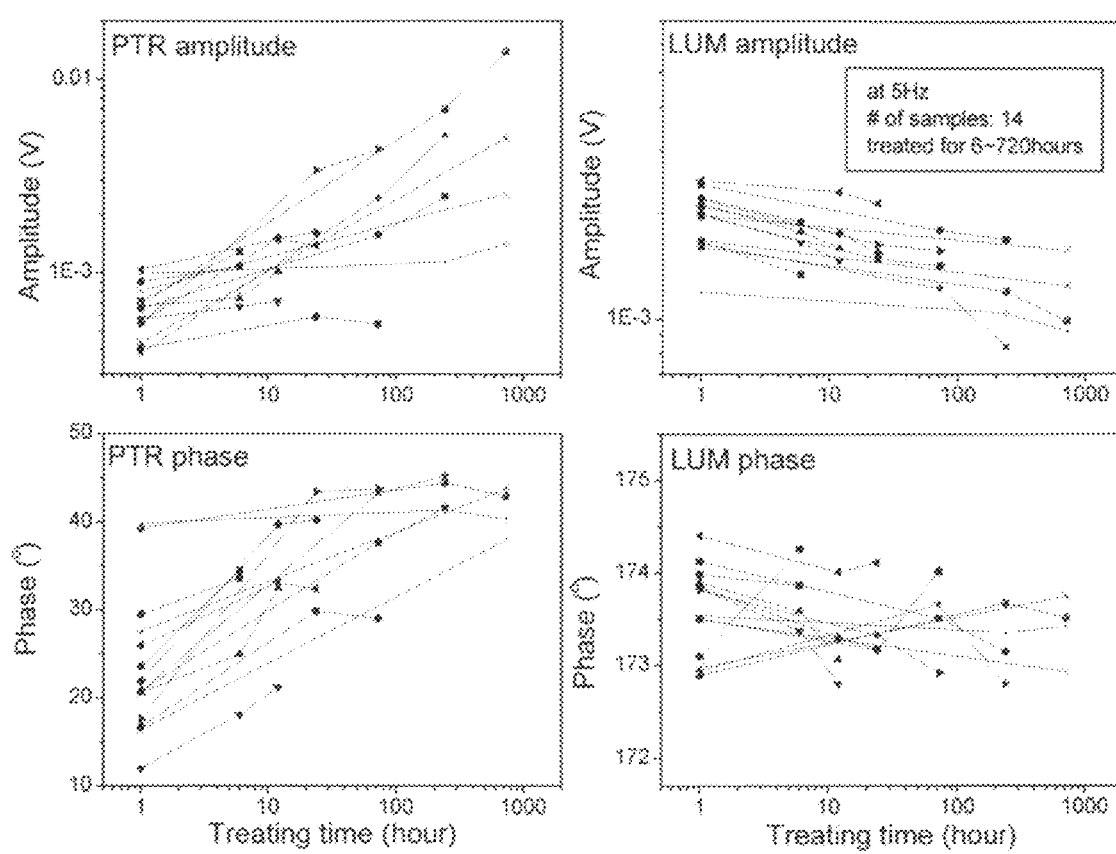
FIG. 5 shows PTR/LUM signals vs. treatment time for multiple samples with treatment time intervals from 6 hours to 30 days at 5 Hz (a) and at 500 Hz (b)
Figure 5B:
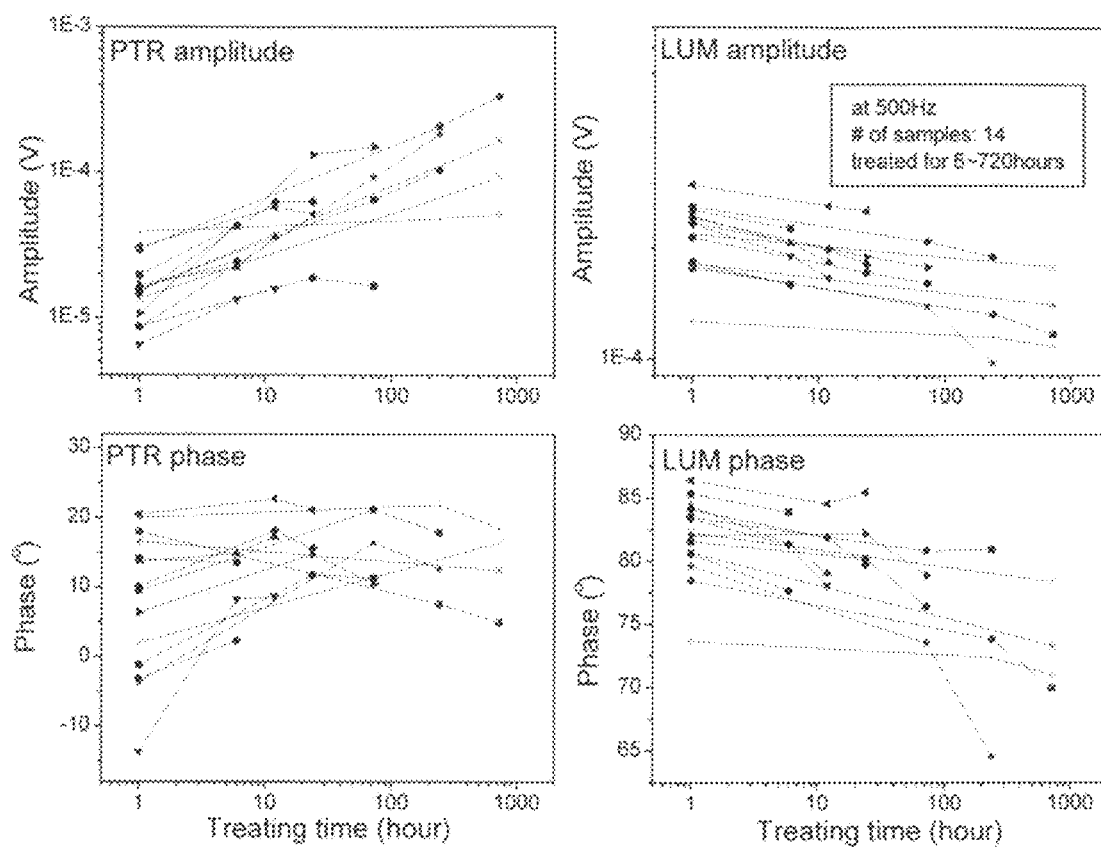

The PTR signals, shown in FIG. 5a and 5b at 5 Hz and 500 Hz, respectively, increased with treatment time while the LUM signals slightly decreased, consistent with trends in FIG. 4. The observed LUM amplitude decreases with increasing degree of demineralization are also consistent with earlier findings in which quantitative light-induced fluorescence (QLF), a form of dc luminescence, was used.

Figure 6A:
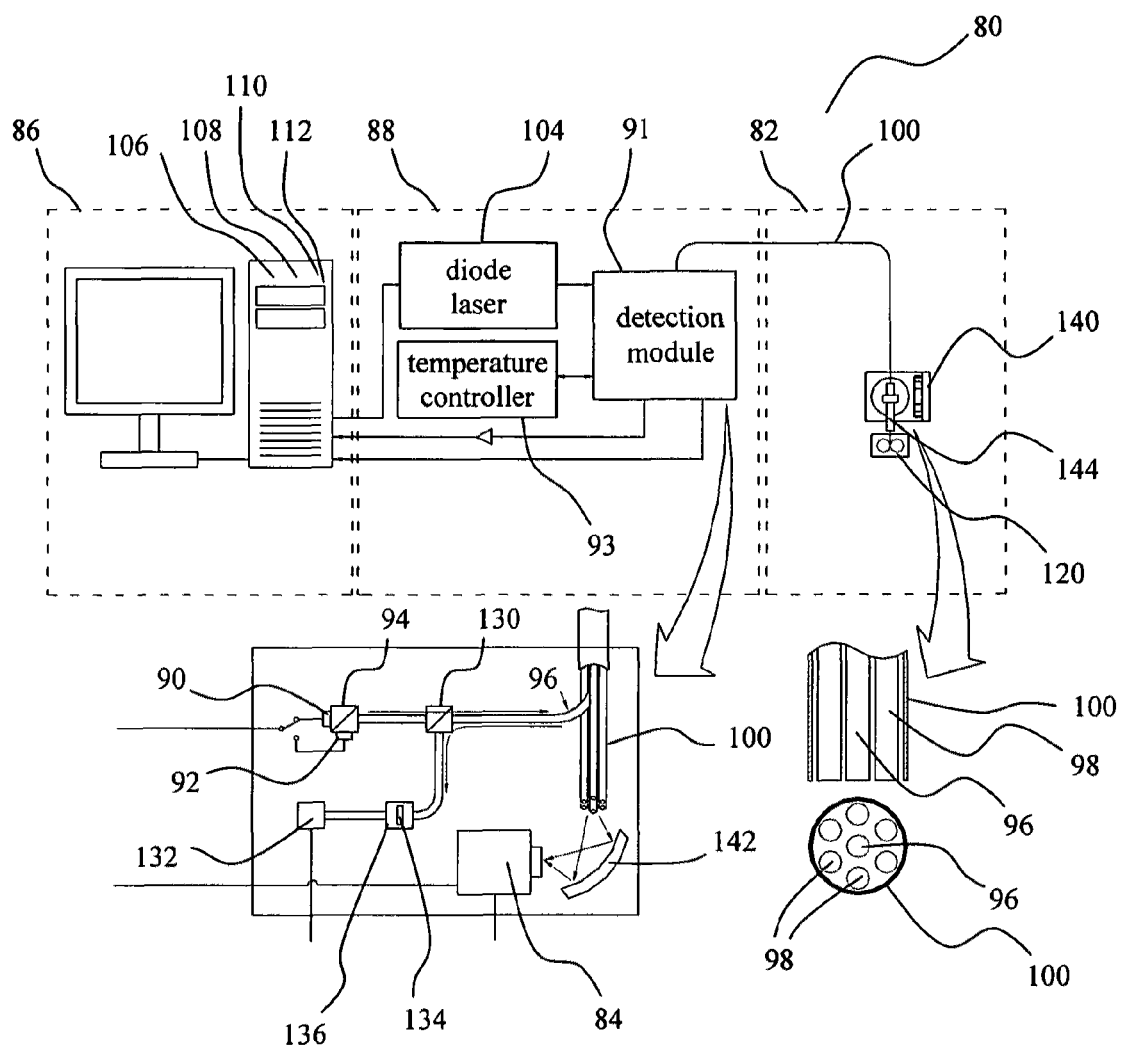
FIG. 6a illustrates a schematic diagram of hand held apparatus for simultaneous frequency domain infrared photothermal radiometry and frequency domain luminescence instrument for detection of defects in teeth which allows for improved compactness and access to occlusal or interproximal, buccal or lingual (smooth surface) or root surface geometries, as well as for substantially enhanced infrared emission collection efficiency using fiber optic light delivery and IR radiation collection instead of the rigid limited-solid-angle collection configuration of off-axis paraboloidal mirrors.

FIG. 6a illustrates an alternative embodiment of an apparatus 80 configuration for interproximal scans involving three distinct modules, 1) a flexible manually controllable fiber optic laser beam delivery/signal collection hand held "optical head" unit 82; 2) a compact electrical and optical power delivery/signal processing unit with room-temperature IR emission detection module 88 which includes a diode laser driver 104 electrically connected to a signal generation and detection module 91 which uses a new state-of-the-art room-temperature mercury-cadmium-zinc-telluride (MCZT) detector 84, and a temperature controller 93 for the detector 84; and 3) a system control and signal analysis unit 86. This detector 84 represents the state-of-the-art in infrared technology. In addition to the mercury-cadmium-zinc-telluride (MCZT) detector, other detectors that could be used include a mercury-cadmium-zinc-telluride (MCZT) detector, a Lead Selenide (PbSe) detector, an Indium Arsenide (InAs) detector, an Indium Antimonide (InSb) detector, and an Indium Gallium Arsenide (InGaAs) detector.

Referring to the detailed view of the detection module 88, one of the two semiconductor lasers 90 and 92 emitting light with a wavelength of 670 nm (e.g. maximum power 500 mW; Photonics Products) and 830-nm respectively (e.g. maximum power 100 mW; Optima Precision) is used as the PTR/LUM sources coupled by an optical coupler 94 and optical fiber 96 optically coupled to the coupler 94 at one end thereof into an optical fiber bundle 100 which includes in addition to fiber 96, several multi-mode, large diameter core silver halide optical fibers (e.g. Ceramoptec) 98 through a multi-channel fiber-optic coupler design (e.g. OZ Optics) which is optically coupled to the hand held optical head 82 at the other end thereof.

Figure 6B:
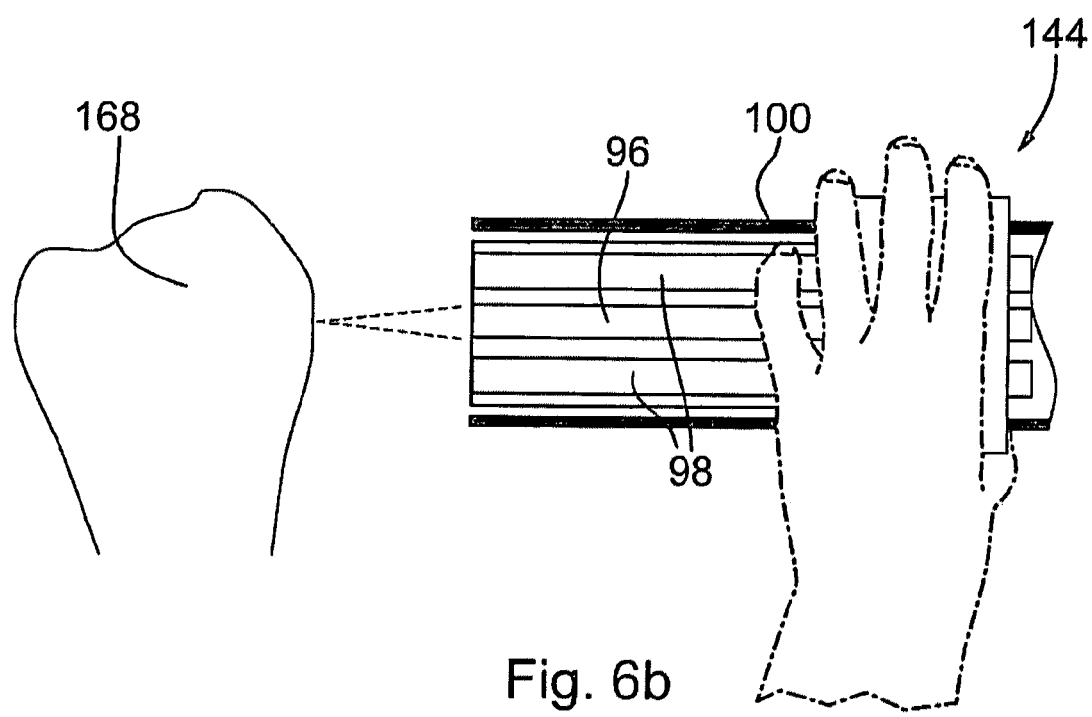

The optical fiber bundle 100 terminates in an optical end section 144 which is a hand held piece mounted to a micro-positioner 140 comprised of a 3-axis translation stage and a rotation stage to hold the fiber-optic end section 144 so that one can control the position of the sample precisely with resolution better than 5 µm. This precise positioning device is for only laboratory experiments for research, and for clinical application, only the hand held piece 144 is used by a clinician who moves this hand piece 144 around a suspicious tooth in a patients' mouth. A blown-up view of the hand held piece 144 is illustrated in FIG. 6*b*.

Other more effective future combinations of laser lines and powers which are or will become apparent to those skilled in the art are also possible, depending on evolving laser technology and are claimed within this disclosure.

The use of two laser light sources at two different wavelengths is advantageous in order to facilitate the interpretation of data. The two-wavelength sources represent different optical penetration depths controlled by the total extinction coefficient associated with each wavelength, a function of the optical absorption and reduced scattering coefficient of enamel (or other dental tissue). Studies by the inventors using thermocouples inside the pulp chamber of teeth irradiated by a 450-mW 670-nm laser showed temperature increases~1° C. Such levels of temperature rise are deemed safe for clinical use and will not cause harm to the pulp tissue of the tooth while yielding acceptable PTR signal-to-noise ratios (~5-80).

Very recent deep caries scanning measurements with these types of laser diodes have shown that PTR with the 830-nm source exhibits higher spatial resolution of sub-surface caries than a 659-nm source at a price of a lower signal level [Jeon R J, Mandelis A, Sanchez V, and Abrams S H., "Non-intrusive, Non-contacting Frequency-Domain Photothermal Radiometry and Luminescence Depth Profilometry of Carious and Artificial Sub-surface Lesions in Human Teeth", *J Biomed Opt*. 9:804-819 (2004), Jeon R J, Han C, Mandelis A, Sanchez V, and Abrams S H., "Diagnosis of Pit and Fissure Caries Using Frequency-Domain Infrared Photothermal Radiometry and Modulated Laser Luminescence", *Caries Res*. 38:497-513 (2004)]. On the other hand, for acid etched lesions or erosions on the enamel surface incurred after a short exposure to an enamel-etching agent, the shorter wavelength source offers higher PTR signal contrast due to the shorter optical extinction depth (a few micrometers). The detection and monitoring of these erosion type lesions is another application of this technology. The diode laser driver 104 (e.g. Coherent 6060, FIG. 1) is used to harmonically modulate the semiconductor laser current (and thus the power output) at a range of 1 Hz to 1000 Hz, triggered by the function generator of a software lock-in amplifier consisting of a PC Board [e.g. NI PCI-5122 (signal analyzer 106 and e.g. NI PCI-5401 (function generator 108] and the appropriate software 110 (e.g LabVIEW). A fast enough computer 112 is required for processing the signals. Laser driver 104 drives only one laser at a time, and as can be seen in FIG. 6 there is a switch for coupling laser driver 104 to one laser or the other separately.

The laser light will be delivered to the dental sample or tooth 120 (for example a dentist using the hand held unit 144 to illuminate a patients tooth) through placing the end of the optical fiber bundle 100 in very close proximity to the dental sample or tooth 120 so that the dental sample is illuminated by one of the two wavelengths of laser light emitted from the distal end of optical fiber 96 located in the hand held head probe 82. The modulated near-infrared LUM signal from the tooth 120 will be collected by the same delivery optical fiber 96 through the reverse splitter 130 to the active area of a Si photodiode 132. However it will be understood that other optical fibers besides fiber 96 could be used to collect the modulated near-infrared LUM signal from the tooth 120. For example, one or more fibers identical to fiber 96 may be included in fiber bundle 100 and fiber 96 could be dedicated to simply delivering the laser light to the tooth and these other fibers identical to fiber 96 could be used to collect the modulated LUM signals and they could have proximal ends optically coupled to detector 132 without the need for reverse splicer 130.

As well, other detectors besides the Si photodiode 132 may be used, including any semiconductor-based photocell with bandgap narrower than the luminescence photon energy, and any other optoelectronic energy conversion device such as a photomultiplier or any detector of luminescence photons, which may include a Germanium (Ge) photodiode, an Indium Gallium Arsenide (InGaAs) photodiode, or a Lead Sulfide (PbS) photodiode.

A cut-on colored glass filter 134 (e.g. Oriel 51345, cut-on wavelength: 715 nm) is placed in a U-bracket 136 in front of the photodetector 132 for LUM measurements generated by the 670-nm laser, to block laser light reflected or scattered by the tooth 120.

Apparatus 80 may include beam expansion and focusing optics for adjusting a size of the beam exiting the optical fiber attached to the end of the fiber for adjusting a size of the area of dental tissue being imaged.

No luminescence data are possible under 830-nm excitation, since photoluminescence emission requires irradiation with higher energy (shorter wavelength) photons than the peaks of luminescence at ca. 636, 673 and 700 nm. The PTR signal are therefore collected by a concentric array of six silver halide or other suitably transparent infrared optical fibers 98 and will be directed to the MCZT detector 84 using elliptic optics 142 with no intervening IR lens elements, for maximum IR power transmission. Infrared focusing optical elements other than mirrors are also possible which will be known to those skilled in the art.

For the occasional measurement of modulated laser power to test for systematic drift through reflectance, the reflected source power will be collected by removing the filter 134 from the same Si photodetector 132 onto which the core light delivery fiber 96 is focused. For monitoring modulated reflectance or luminescence, a second channel of the software lock-in amplifier 106 will be used.

At each measurement, a PTR/LUM frequency and/or spatial coordinate scan can be performed with this instrument. Frequencies can be varied from 0.1 Hz to 1 kHz or higher, ensuring thermal diffusion lengths in the range 12 µm -1 mm [Jeon R J, Mandelis A, Sanchez V, and Abrams S H., "Non-intrusive, Non-contacting Frequency-Domain Photothermal Radiometry and Luminescence Depth Profilometry of Carious and Artificial Sub-surface Lesions in Human Teeth", *J Biomed Opt* 9:804-819 (2004)]. This range of sub-surface depths accessible photothermally assures our ability to monitor deep carious lesions or demineralization below a thin remineralized superficial layer of enamel. Using a micro-positioner 140 composed of a 3-axis translation stage and a rotation stage to hold the fiber-optic bundle 100, one will be able to control the position of the sample precisely with resolution better than 5 µm.

As discussed above with respect to the device of FIG. 1, the modulated PTR and LUM emissions are then demodulated into photothermal phase and amplitude components and said modulated luminescence signals into luminescence phase and amplitude signals by a lock-in amplifier and processed to compare the photothermal phase and amplitude signals to photothermal phase and amplitude signals of a reference sample and comparing the luminescence phase and amplitude signals to luminescence phase and amplitude signals of a reference sample to obtain differences, if any, between the portion of the dental tissue and the reference sample and correlating these differences with defects in the dental tissue. Further details are disclosed in U.S. Pat. No. 6,584,341 issued Jun. 24, 2003 to Mandelis et al. which is incorporated herein in its entirety by reference.

The step of comparing includes normalizing the photothermal amplitude signals and the luminescence amplitude signals by ratioing photothermal amplitude signals at least two different frequencies, ratioing luminescence amplitude signals at these two different frequencies, and taking the difference of photothermal phase signals at the two frequencies and taking a difference of luminescence phase signals at the two different frequencies to cancel effects of light source intensity fluctuations and instrumental frequency dependence.

The step of comparing also includes generating a baseline signal transfer function, H(f), by obtaining frequency-scan data from the reference sample with known radiometric and dynamic (ac) luminescence properties and frequency response, and comparing the portion of a surface and the known healthy portion of a tooth by means of ratios of photothermal amplitudes, ratios of luminescence amplitudes, and phase differences between photothermal phases and luminescence phases at different frequencies for cancellation of the instrumental frequency response.

The step of demodulating the emitted photothermal signals into photothermal phase and amplitude components and the luminescence signals into luminescence phase and amplitude signals is done using a lock-in amplifier and the instrumental frequency dependence is the lock-in amplifier response. The reference sample may be a known healthy portion of a tooth or other dental tissue depending on the tissue being examined.

The apparatus of FIG. 6 is very useful for examining portions of a tooth for example, and the size of the spot is determined by core of the fiber, the presence or absence of focusing optics at the end of the fiber (e.g. selfoc lenses) and the distance of the emerging light beam from the tooth surface. Under normal operation of the instrument the optical fiber bundle will be in contact with dental surface under examination. Increasing or decreasing the beam diameter allows a clinician to examine an occlusal fissure and negate the influence of fissure geometry or angulation. With a wider beam one can detect a signal from a wider area of the fissure.

Figure 7:
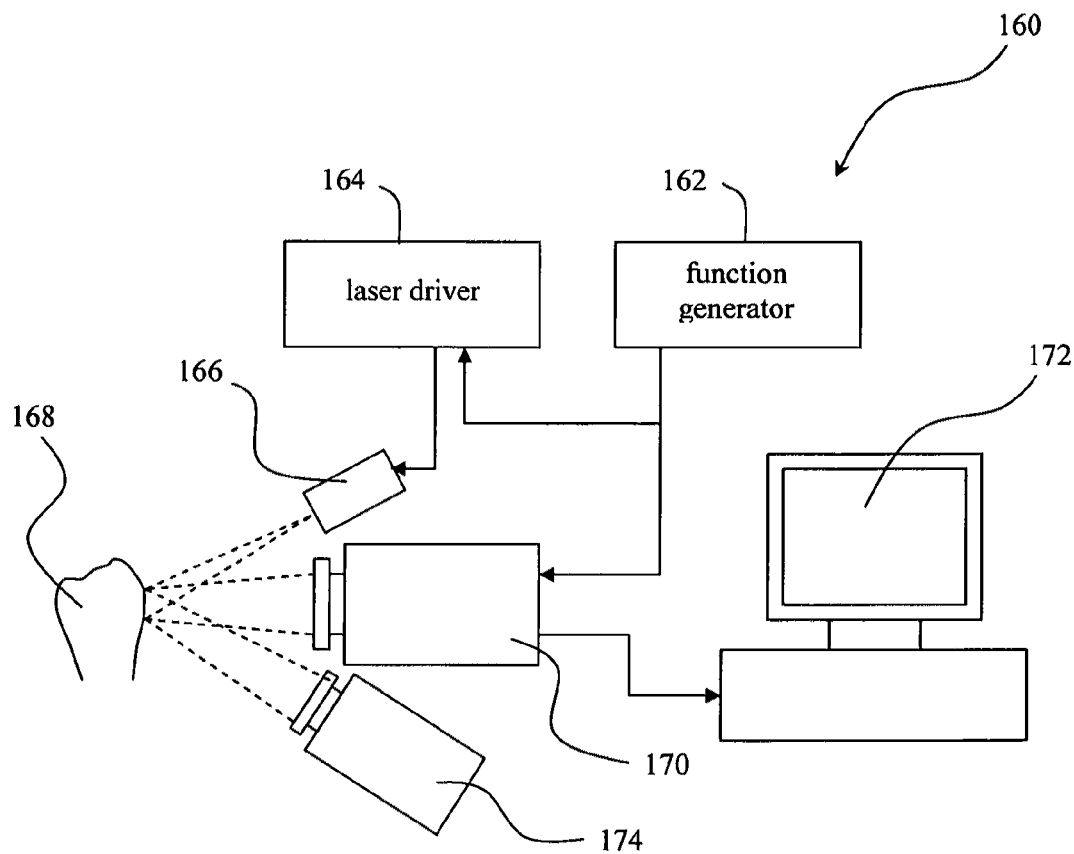
FIG. 7 illustrates a schematic diagram of two dimensional lock-in imaging system by means of modulated infrared cameras.

FIG. 7 illustrates a modulated infrared lock-in imaging system shown generally at 160. Function generator 162 provides modulated sinusoidal waveform to the laser driver 164 to supply modulated current to the laser 166 that is a light source appropriately expand so as to excite a desired area of the surface of a sample of dental tissue 168.

PTR and LUM signals are collected by a combined infrared camera 170 (a near infrared camera such as InGaAs for ac luminescence and a mid infrared camera such as HgCdTe for photothermal detection) which is triggered by the function generator 162 to be synchronized with the laser driver 164.

Camera 170, like any camera (film or digital), includes a lens or combination of lenses to project an image onto a detector array. Images are composed of multiple pixels. The detector array in the modulated IR camera is similar to the image cell in a digital camera. Each detecting element (pixel) will generate a signal due to excitation by photons. In the present application, the signal is being modulated, so it is an AC signal. The AC signals are sent to the computer 172 which is equipped with a lock-in amplifier, such that the computer demodulates the signals which are sent from camera 170, pixel by pixel, into two components; amplitude and phase. Then these signals, amplitude and phase, are used to create a visible image on the monitor for observation by the clinician.

Entire images from the cameras are collected at a rate at least double that required by the sampling theorem (4 images/modulation period) and stored in the computer, each image averaged over a suitable number of periods. Lock-in software applied to those images yields amplitude and phase images displayed on the computer screen by the operator. These signals from the cameras sent to the computer 172 show two dimensional lock-in images at the modulation frequency of the laser.

Particularly, the images of the emitted modulated photothermal signals from the camera 170 are demodulated into signals of photothermal phase and amplitude components and the images of modulated luminescence signals are demodulated into signals of luminescence phase and amplitude signals. The demodulated signals are converted into images and then comparing the images of photothermal phase and amplitude signals to images of photothermal phase and amplitude signals of a reference sample and comparing the images of luminescence phase and amplitude signals to images of luminescence phase and amplitude signals of a reference sample to obtain differences, if any, between the portion of the dental tissue and said reference sample and correlating the differences with defects in the dental tissue.

In addition to using an infrared camera 170, in another embodiment of the imaging apparatus a modulated visible light camera 174 (preferably a CCD camera) can also be used in addition to the IR camera 170 which allows images of the tooth at visible wavelengths to be recorded. An advantage of this combination is that it provides better control of where the laser beam is located on the tooth and for the IR camera shot the clinician wants to take of the tooth or root surface under inspection. Modulated visible cameras may be used to do phase-locked LUM imaging, in addition to the lock-in PTR imaging. An advantage of using CCD visible range camera 174 is that it provides the clinician with an image of the tooth or root surface under examination and allows a clinician to mark on the image the areas that need to be examined. This provides the clinician with a permanent record of areas that need to monitored on a long term basis. Colour changes, especially the appearance of white or brown spots could indicate the presence of demineralized or remineralized enamel lesions. Once located and stored the clinician can then monitor changes in PTR and LUM from these areas as well as provide the patient with a printout of the areas in question.

The conventional CCD camera 174 may be used in the dc mode for monitoring the position and exact location of the region to be probed photothermally. In addition, the same camera with suitable optical filters to exclude contributions outside the LUM spectral range (700 to 850 nm) can be used in a modulated mode to generate LUM images at some suitable frequency as explained in the margin above; with a switchover of the controlling computer software.

Thus, the apparatuses disclosed herein provide a very useful method for addressing important dental problems such as the detection and or diagnosis of smooth surface lesions, occlusal pits and fissure lesions and interproximal lesions between teeth which normally go undetected by x-ray radiographs and visual examination. The instrument is also able to detect early areas of demineralized tooth or root and or areas of remineralized tooth or root as well as defects along the margins of restorations including crowns, inlays, fillings etc. The instrument shown in FIG. 6 disclosed herein is capable of inspecting a local spot on a tooth, and the instrument of FIG. 7 is capable of modulated imaging of the sub-surface of a target tooth by using a multi-array infrared camera (FIG. 7). A visible camera is used to monitor changes on the surfaces of the tooth such as white spots and other signs of demineralized or remineralized tooth surface.

Thus, based on the results of scans of a patient's tooth using the apparatus of FIGS. 6 and/or 7, if the clinician detects for example enamel or root caries lesions including both demineralization and remineralization, erosion lesions including both demineralization and remineralization on any of the tooth surfaces, he/she can then monitor the area in question or institute corrective measures to treat the tooth by using lasers to i) remove the decayed or carious tooth material, ii) prepare the tooth using known principles of tooth preparation design, iii) alter the surface using a laser, iv) alter the surface to allow the uptake of various media to enhance remineralization, v) apply a medium that will either seal the surface or promote remineralization of the surface, vi) cure or set a material on the tooth surface restoring the tooth to form and function, using suitable laser-fluence delivery protocols through pulse-waveform engineering, for precise, optimized control of optical radiation delivery and thermal energy generation.

During this process of carrying out these various corrective steps to restore the tooth, the clinician may be monitoring the dental tissue during these interventional alterations in the condition of the tooth by means of combined PTR and LUM using the apparatus of FIG. 6 or 7.

The devices disclosed herein using combined PTR/LUM can be combined with other detection systems such as Digital Fibre Optic Transillumination (DIFOTI), Quantitative Laser Fluorescence (QLF), Optical Coherence Tomography (OCT) and or Electrical Caries Resistance Monitoring (ECM) to provide additional information on the status of the lesion or defect being examined. Each of these techniques mentioned, have existing descriptions in the literature on how they detect lesions and their various shortcomings. QLF is able to detect luminescence throughout the entire depth of the enamel surface to the junction with the next layer or dentin. The colour change in luminescence is used to detect and monitor demineralization and remineralization. QLF is not capable of any depth profilometric examination but can monitor the change in size of the lesion as long as the tooth surface reference points do not change in their orientation.

Electrical Caries Resistance monitors the change in electrical potential across a dry tooth surface. The technique is described in the literature and requires a dry field for monitoring. It is currently not able to provide any depth information about a carious lesion or area of demineralization.

Furthermore, the current laboratory apparatus can be used to detect and monitor artificially created lesions and or natural lesions in vitro. This can then be used to test in vitro the effects of various techniques, materials or substances to create erosive lesions, demineralized lesions or artificial carious lesions on tooth surface including the root surface. In addition, PTR and LUM can then be used to detect changes in these lesions induced by the application of various substances. PTR and LUM can be used to detect the amount and extent of demineralization and or remineralization after the application of various substances to the tooth or root surface. PTR can then be combined with other sensitive but destructive techniques such as MicroCT and TMR to measure lesion changes and provide a visual representation of the lesions.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

TABLE 1

Diagnostic criteria for the Visual Inspection, DIAGNOdent, X-ray and Histological Observation

| General Description of Levels of Caries | Visual Inspection (1~10) | DIAGNOdent (0~99) [Lussi et al. Caries Res, 1999] | Radiograph | Histological Observation |
|---|---|---|---|---|
| $D_0$: Intact | | | Healthy: Indicating no sign of demineralization | Sound enamel or Healthy fissure |
| $D_1$: no caries, or histological enamel caries limited to the outer half of the enamel thickness | 1~2 Incipient or Healthy Fissures Observe & Monitor | 0-4 | Enamel caries under ½ the distance to DEJ | Demineralized fissure but solid enamel base; very good enamel thickness to the pulp; at least ½ thickness of enamel remains intact |

TABLE 1-continued

Diagnostic criteria for the Visual Inspection, DIAGNOdent, X-ray and Histological Observation

| General Description of Levels of Caries | Visual Inspection (1~10) | DIAGNOdent (0~99) [Lussi et al. Caries Res, 1999] | Radiograph | Histological Observation |
|---|---|---|---|---|
| $D_2$: histological caries extending beyond the outer half, but confined to the enamel | 2~5 Fissures are suspect. Fissure Sealant recommended | 4.01~10 | Enamel caries greater than ½ the distance to DEJ | Demineralized fissure but solid enamel base |
| $D_3$: histological dentinal caries limited to the outer half of the dentin thickness | 6~8 Restore the Fissure with direct placed restoration | 10.01~18 | Dentin caries | Caries into dentin |
| $D_4$: histological dentinal caries extending into the inner half of dentin thickness | 9~10 Deep Dentin Caries Large carious lesions | >18.01 | | |

TABLE 2

Characteristics of frequency scan curves of PTR and LUM

| Signal | General characteristics | Converting equation to determine numeric ranking |
|---|---|---|
| PTR amplitude | The shape for a healthy spot in log-log plot is almost linear from low frequency (1 Hz) to high frequency (1000 Hz). Unhealthy (demineralized surface, enamel caries or dentin caries) spots show greater amplitude at all frequency ranges compared to healthy spots. Unhealthy spots show a curvature (greater than healthy spots) in the frequency range of 10~100 Hz in a logarithmic plot. | (slope at low frequency) − (slope at high frequency) average of 4 frequencies |
| PTR phase | The shape for the healthy spot in log (freq.) - linear (phase) plot is almost linear from low frequencies (1 Hz) to high frequencies (1000 Hz). Unhealthy spots show higher phase at low frequency range and the reverse at the high frequency range than healthy spots. | (average of phases at 2 low frequencies (1, 6.68 Hz)) − (average of phases at 2 high frequencies (211.35, 1000 Hz)) |
| LUM amplitude | Both healthy and unhealthy spots show same shape: higher amplitude at low f than at high f. Unhealthy spots show greater amplitude than healthy ones. | average at 3 frequencies (1, 211.35, 501.18 Hz) |
| LUM phase | High frequency range (>100 Hz) only, unhealthy spots show larger phase than healthy ones. | one phase signal at high frequency (501.18 Hz) |

TABLE 3

Sensitivities and specificities at the caries level of enamel ($D_2$) and the caries level of dentin ($D_3$) for various examination methods

| Examination method | Sensitivity threshold ($D_2/D_3$) | Specificity threshold ($D_2/D_3$) | Size of sample (# of points) |
|---|---|---|---|
| PTR and LUM combined | 0.81/0.79 | 0.87/0.72 | 280 |
| PTR only | 0.69/0.52 | 0.86/0.72 | 280 |
| LUM only | 0.61/0.58 | 0.81/0.77 | 280 |
| Visual Inspection | 0.51/0.36 | 1.00/1.00 | 52 |
| Radiograph | 0.29/0.36 | 1.00/0.85 | 52 |
| DIAGNOdent | 0.60/0.76 | 0.78/0.85 | 131 |

Therefore what is claimed is:

1. A modulated imaging system for imaging dental tissue using modulated photothermal radiometry and luminescence, comprising:
   a function generator configured to provide a modulation waveform;
   at least one laser light source for irradiating a portion of a surface of a dental tissue with a beam of light of an effective wavelength, wherein laser light from said at least one laser light source is modulated according to said modulation waveform, and wherein modulated photothermal radiometric signals and modulated luminescence signals are responsively emitted from said portion of the surface;
   a mid-infrared camera for imaging said modulated photothermal radiometric signals and generating photothermal images, wherein the generation of the photothermal images by said mid-infrared camera is triggered according to said modulation waveform;
   a near-infrared camera for imaging said modulated luminescence signals and generating luminescence images, wherein the generation of the luminescence images by said near-infrared camera is triggered according to said modulation waveform; and
   a computing device including a software-based lock-in amplifier, wherein said computing device is configured to:
   collect, from said mid-infrared camera, a plurality of photothermal images during at least one modulation cycle of the modulation waveform, wherein the photothermal images are collected at a rate of at least four images per modulation cycle;
   collect, from said near-infrared camera, a plurality of luminescence images during at least one modulation cycle of the modulation waveform, wherein the luminescence images are collected at a rate of at least four images per modulation cycle;
   process the photothermal images with said software-based lock-in amplifier and demodulate the photothermal images into a photothermal phase image and a photothermal amplitude image; and
   process the luminescence images with said software-based lock-in amplifier and demodulate the luminescence images into a luminescence phase image and a luminescence amplitude image.

2. The modulated imaging system according to claim 1 wherein said at least one laser light source includes a laser driver, and wherein said function generator is synchronized with said laser driver.

3. The modulated imaging system according to claim 1 wherein said near-infrared camera is an InGaAs camera, and said mid-infrared camera is an HgCdTe camera.

4. The modulated imaging system according to claim 1 further comprising beam expansion and focusing optics for adjusting a size of said beam of light incident on the dental tissue for adjusting a size of the area of dental tissue being imaged.

5. The modulated imaging system according to claim 1 further comprising a visible-wavelength camera for recording images of the dental tissue at wavelengths in a visible portion of the spectrum.

6. The modulated imaging system according to claim 5 wherein said visible-wavelength camera is a CCD (charge coupled device) camera sensitive in the visible portion of the spectrum.

* * * * *